US007981852B2

(12) United States Patent
Yang et al.

(10) Patent No.: US 7,981,852 B2
(45) Date of Patent: Jul. 19, 2011

(54) METHOD OF ENHANCING PERFUME RETENTION DURING STORAGE USING LOW TOTAL FATTY MATTER EXTRUDED BARS HAVING STARCH POLYOL STRUCTURING SYSTEM

(75) Inventors: Lin Yang, Woodbridge, CT (US); Georgia Shafer, Southbury, CT (US); Ricardo-Neri Da Silva, San Paulo CEP (BR); Sergio Roberto Leopoldino, Sao Paulo (BR)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/639,077

(22) Filed: Dec. 16, 2009

(65) Prior Publication Data

US 2011/0143985 A1 Jun. 16, 2011

(51) Int. Cl.
*A61K 7/50* (2006.01)

(52) U.S. Cl. ......... 510/141; 510/146; 510/152; 510/155

(58) Field of Classification Search ........................ None
See application file for complete search history.

(56) References Cited

U.S. PATENT DOCUMENTS

| | | | | |
|---|---|---|---|---|
| 6,194,362 | B1 | 2/2001 | Trinh et al. | 510/101 |
| 6,207,636 | B1 | 3/2001 | Benjamin et al. | 510/458 |
| 6,310,016 | B1 | 10/2001 | Behal et al. | 510/152 |
| 6,336,553 | B1 | 1/2002 | Gordon | 206/77.1 |
| 6,440,908 | B2 | 8/2002 | Racherla | 510/122 |
| 6,852,681 | B1 * | 2/2005 | Kerschner et al. | 510/152 |
| 6,858,574 | B2 | 2/2005 | Yang et al. | 512/1 |
| 6,998,382 | B2 | 2/2006 | Yang et al. | 512/1 |
| 7,030,068 | B2 | 4/2006 | Clare et al. | 510/101 |
| 2006/0281650 | A1 * | 12/2006 | Keenan et al. | 510/141 |
| 2007/0021314 | A1 | 1/2007 | Salvador et al. | 510/151 |
| 2007/0155639 | A1 | 7/2007 | Salvador et al. | 510/141 |
| 2007/0280976 | A1 | 12/2007 | Taylor | 424/401 |

FOREIGN PATENT DOCUMENTS

| | | |
|---|---|---|
| EP | 0 088 846 | 3/1986 |
| EP | 1 656 441 | 11/2010 |
| GB | 2459093 | 10/2009 |
| JP | 10-60482 | 3/1998 |
| WO | 95/26710 | 10/1995 |
| WO | 96/35772 | 11/1996 |
| WO | 98/18896 | 5/1998 |
| WO | 01/42418 | 6/2001 |
| WO | 03/010272 | 2/2003 |
| WO | 2005/080541 | 9/2005 |
| WO | 2006/094586 | 9/2006 |
| WO | 2010/089269 | 8/2010 |

OTHER PUBLICATIONS

Co-pending Application: Applicant: Yang et al., U.S. Appl. No. 12/639,113, filed Dec. 16, 2009.

* cited by examiner

*Primary Examiner* — Necholus Ogden, Jr.
(74) *Attorney, Agent, or Firm* — Ronald A. Koatz

(57) ABSTRACT

The present invention relates to a method of enhanced perfume retention, e.g., bars providing enhanced retention. By selecting specific bar compositions (e.g., with low TFM and specific starch-polyol structuring system), it has been unexpectedly found that retention of perfume during dry bar storage is actually increased.

4 Claims, No Drawings

METHOD OF ENHANCING PERFUME RETENTION DURING STORAGE USING LOW TOTAL FATTY MATTER EXTRUDED BARS HAVING STARCH POLYOL STRUCTURING SYSTEM

FIELD OF THE INVENTION

The present invention relates to extruded bars having relatively low amounts of total fatty matter, in particular to such bars comprising perfume.

BACKGROUND OF THE INVENTION

The percentage of perfume retained in the headspace over a bar surface (specifically, the perfume headspace concentration, after storage, divided by perfume headspace concentration at initial time zero) measured after storage at 50° C. for one month can be defined as "perfume headspace retention". Enhanced retention in a bar is important because it is correlated with enhanced fragrance activity that perceived by consumers, presumably because less perfume (especially top note perfume elements) is lost.

There are a number of references relating to fragrance loss.

U.S. Pat. No. 6,336,553 to Gordon discloses packages that prevent fragrance or moisture loss during storage.

JP 10060482 to Givaudan Roure Int. discloses a perfume carrier comprising a solid water-insoluble inorganic carrier, a perfume composition, a perfume thickener soluble in water, and a perfume for limiting the loss of a perfume during storage of a bar.

Various references relate to reducing overall soap level (total fatty matter, TFM) using structuring technology. These references include as follows:

WO 01/42418 to Chokappa et al. discloses a detergent bar containing 0.5 to 30% amorphous alumina, one alkali metal salt of carboxylic/sulfonic acid, 5-70% detergent active and 10-55% water.

U.S. Pat. No. 6,207,636 to Benjamin et al. discloses detergent bars having 25-70% total fatty matter, 9-16% by weight colloidal aluminum hydroxide and 12-52% water. The invention also comprises a process for preparing a detergent bar.

WO 2006/094586 to Gangopadhayay et al. discloses a low TFM detergent bar including soap (15% to 30% TFM); 25% to 70% inorganic particulates including talc and calcium carbonate; 0.5% to 10% of alumino-silicate; and 3% to 20% water.

U.S. Pat. No. 6,310,016 to Behal et al. discloses a detergent bar including soap (15-70% total fatty matter); 0.5-40% colloidal aluminum hydroxide-phosphate complex, and 10-50% water. A process for making such bars is also disclosed.

U.S. Pat. No. 6,440,908 to Racherla discloses high moisture containing bar compositions that includes a borate compound. The borate compound structures water in the bar thereby enabling the retention of high amounts of moisture without compromising bar properties.

WO 2005/080541 to Gangopadhayay et al. discloses a non-granular solid cleaning composition comprising 50% to 70% of a salt of fatty acid; 1% to 15% of a mono- or disaccharide; and 0.02% to 2% of a stabilizing agent. Preferred saccharides are glucose, sucrose, mannose, and fructose and the stabilizing agent is preferably chosen from the class of fungicides including formaldehyde, benzoic acid and salts thereof and methyl or ethyl paraben.

WO 03/010272 to Anderson et al. discloses soap or detergent bar having relatively low levels of total fatty matter (40% to 78%), allowing relatively high levels of water (7% to 30%) and/or other liquid additives to be present by incorporating aluminum hydroxide and tetra sodium pyrophosphate decahydrate into the bar. Methods of producing such bars are also disclosed.

WO 96/35772 to Wise et al. discloses laundry bar compositions including from about 20% to about 70% surfactant; from about 12% to about 24% water; from about 6.25% to about 20% calculated excess alkali metal carbonate; from about 2% to about 20% water-soluble inorganic strong-electrolyte salt; and various optional ingredients including whole-cut starch.

WO 95/26710 to Kacher et al. discloses personal washing bar compositions that include about 5 parts to about 40 parts of a lipid skin moisturizing agent; about 10 parts to about 50 parts of a rigid crystalline skeleton network structure consisting essentially of selected fatty acid soap or a mixture of said soap and selected fatty acid; about 1 part to about 50 parts of a lathering synthetic surfactant, and; about 10 parts to about 50 parts water.

WO 98/18896 to Rahamann et al. discloses high moisture laundry bar composition including from about 45% to about 95% structured soap composition, wherein said structured soap composition comprises a premixture of from about 45% to about 75% soap; from about 5% to about 50% starch; about 25% to about 45% moisture; and wherein the ratio of starch to moisture in said structured soap composition is from about 1:5 to about 1.25:1; and from about 1% to about 15% synthetic anionic surfactant; wherein the total moisture in the finished bar composition is from about 20% to about 40%.

U.S. Patent Nos. 2007/0021314 and 2007/0155639 to Salvador et al. disclose cleansing bar compositions having high water content that include (a) at least about 15% by weight of the composition of water; (b) from about 40% to about 84% by weight of the composition of soap; and (c) from about 1% to about 15% by weight of the composition of inorganic salt. The bar compositions further comprise a component selected from the group consisting of carbohydrate structurant, free fatty acid, synthetic surfactants, and mixtures thereof. The bar compositions preferably have a Water Activity ("Aw") of less than about 0.95, preferably less than about 0.90, and more preferably less than about 0.85. The bar compositions are preferably manufactured by a milling process.

In general, when the predominant surfactant in the personal washing bar is fatty acid soap, a reduction in surfactant is commonly expressed as reduction in "Total Fatty Matter" or TFM. The term TFM is used to denote the percentage by wt. of fatty acid and triglyceride residues present in soaps without taking into account the accompanying cations. The measurement of TFM is well known in the art. A "low" TFM bar is typically one which will have <70%, preferably <65%, more preferably <60% and even more preferably <55% TFM.

There are references which do disclose generally extruded bars with low TFM and comprising structuring systems like those of the invention. GB Application No. 806340.6 to Leopoldino (Unilever), filed Apr. 8, 2008, for example, discloses low TFM extrudable soap bar compositions which include starch, polyols and optionally water insoluble particles. Perfume is an optional ingredient which is recited in a long list of many, many possible optionals and there is no disclosure or suggestion that there is any benefit (i.e., enhanced perfume retention) to using perfume in such bar compositions relative to any other bar compositions.

As indicated, applicants have filed copending Great Britain Application No. 0806340.6 to Leopoldino et al., entitled "Extruded Soap Bars Comprising a Composite Starch-polyol Structuring System". Applicants have also filed Great Britain Application No. 0901953.0 to Canto et al., entitled "Low TFM Extruded Soap Bars Comprising Starch Polyol Structuring System".

Neither reference discloses or recognizes the unexpected enhanced perfume storage retention which occurs when using low TFM starch-polyol bars relative to other bar compositions.

Quite unpredictably, however, applicants have found that, when perfume is used in such specific, low TFM, starch-polyol structured systems (comprising, for example, 5 to 30% preferably 6 to 25% by wt. polyol), there is found enhanced perfume retention during storage when compared to, for example, effect of the same perfume used in soap bars having >60% by wt. fatty acid soap.

While not wishing to be bound by theory, applicants believe that polyols (required for reducing TFM using starch-polyol structuring system) are good solvents for the perfume oils and, because the perfume is dissolved, this typically results in lower perfume headspace over the bar. This "suppression" also means, however, that less perfume is lost into the vapor phase during storage. It is believed that this "suppression" effect of polyols on perfume headspace disappears when the bar is diluted. Thus, quite unpredictably, the use of high polyol level in the low TFM starch-polyol system actually ends up retaining more fragrance during storage than conventional bars without starch-polyol system. In higher TFM bars (>60% fatty acid soap), the same enhancement is not observed.

BRIEF SUMMARY OF THE INVENTION

The present invention thus provides for a method of enhancing perfume retention during storage simply, but quite unexpectedly, by formulating into specific bar formulations as defined.

More particularly, the invention is a method for enhancing perfume retention in storage (e.g., relative to the retention if the same perfume were used in soap bar composition having >60 fatty acid soap) by selecting and formulating perfume into extrudable bar compositions comprising:

a) 20 to <60%, preferably 20 to 55% by wt. fatty acid soap;
b) 0.1 to 2.0%, preferably 0.3 to 1.5% water soluble salt of monovalent cation;
c) 0 to 5.0% fatty acid; and
d) structuring system comprising:
   (i) 5 to 30%, preferably 6 to 25%, even more preferably 8 to 20% by wt. polyol (preferably selected from group consisting of glycerol, sorbitol and mixtures thereof);
   (ii) 6% to 30%, preferably 6 to 25% by wt. starch; and
   (iii) 0 to 10% by wt. water soluble particles;

and by then storing the bars in, e.g., a carton box (for bar packaging) as is.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental example, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y" it is understood that all ranges combining the different endpoints are also contemplated. Further in specifying the range of concentration, it is noted that any particular upper concentration can be associated with any particular lower concentration. Where the term "comprising" is used in the specification or clams, it is not intended to exclude any terms, steps or features not specifically recited. For the avoidance of doubt, the word "comprising" is intended to mean "including" but not necessarily "consisting of" or "composed of". In other words, the listed steps, options, or alternatives need not be exhaustive. All temperatures are in degrees Celsius (° C.) unless specific otherwise. All measurements are in SI units unless specified otherwise. All documents cited are—in relevant part—incorporated herein by reference.

DETAILED DESCRIPTION OF THE INVENTION

The present invention relates to a method of enhancing perfume retention during storage (defined by storage at 50° C. for one month) by selecting and formulating the perfume into specific bar formulations. Unexpectedly, applicants have discovered that, when perfumes are formulated into low TFM (i.e., 20% to less than 60%, preferably 20% to 55%, even more preferably 20% to 50% fatty acid soap) formulations which are structured with starch-polyol structuring system, there is found enhanced perfume retention relative to retention values obtained from "soap structured" soap-based bar compositions.

Specifically, enhanced retention is observed when perfume (preferably less volatile perfumes) is formulated into bar compositions comprising:

a) 20 to less than 60% by wt., preferably 20 to 55% by wt. fatty aid soap;
b) 0.1 to 2.0%, preferably 0.3 to 1.5% added soluble salt of monovalent cation;
c) 0 to 5.0% fatty acid; and
d) structuring system comprising:
   i. 5 to 30%, preferably 6 to 25%, even more preferably 8 to 20% by wt. polyol (preferably selected from group consisting of glycerol, sorbitol and mixtures thereof);
   ii. 6% to 30%, preferably 6 to 25% by wt. starch; and
   iii. 0 to 10%, preferably 1 to 8% by wt. water soluble particles; and
e) then storing the bars in carton box for packaging.

In preferred embodiments, the structuring system comprises:

a) polyol selected from the group consisting of glycerols, sorbitol and their mixtures;
b) 6 to 25% by wt. starch; and
c) optional water insoluble particles;

wherein the sum of the weights of the polyol, starch and water insoluble particles comprises at least 20% but no more than 70% of the bar by wt.; and the bar is an extrudable mass having a yield stress between 350 and 2000 kPa measured at temperature of 40° C.

In one embodiment, optional insoluble particles are inorganic particulates.

The bar may include synthetic surfactant at levels of up to 10% by wt. of the bar, preferably 2% to 8% by wt.

The bar can also include slip modifier which improves the feel of the wet bar when rubbed on the skin, especially when starch and/or insoluble particles are approaching upper levels of their concentration range.

In another embodiment, the composition contains less than 20% preferably 14 to 19% water when the bar is initially made, i.e., immediately after it is extruded and stamped.

The bars used in the method for enhanced retention for storage of the present invention are extruded personal washing bars that comprise specific levels of fatty acid soaps; one or more added soluble salts; optional fatty acid; a structuring system (present at levels from as low as about 20% to as high as 70%, largely depending on the levels of fatty acid soap used) and various other optional ingredients. These components of the bar composition, as well as the method used to manufacture and evaluate the bars, are described below.

The bar compositions of the invention are capable of being manufactured at high production rates by processes that generally involve the extrusion forming of ingots or billets, and stamping or molding of these billets into individual tablets, cakes, or bars.

By capable of high manufacturing rates is meant that the mass formed from the bar composition is capable of (i) being extruded at a rate in excess of 9 kg per minute, preferably at or exceeding 27 kg per minute and ideally at or exceeding 36 kg per minute; and (ii) capable of being stamped at a rate exceeding 100 bars per minute, preferably exceeding 300 bars per minute and ideally at a rate at or above 400 bars per minute.

Furthermore, personal washing bars produced from these composition sat high production rates should possess a range of physical properties that make them entirely suitable for every day use by mass market consumers.

Test method useful in assessing various physical properties of bars manufactured from these composition as to establish criteria for manufacturing capability and consumer acceptability are described below in the TEST METHODOLOGY section.

Bar Composition (Used in Method of Invention)

Fatty Acid Soap

The fatty acid soaps, other surfactants and in fact all the components of the bar should be suitable for routine contact with human skin and preferably yield bars that are high lathering.

The preferred type of surfactant is fatty acid soap. The term "soap" is used herein in its popular sense, i.e., the alkali metal or alkanol ammonium salts of aliphatic, alkane-, or alkene monocarboxylic acids. Sodium, potassium, magnesium, mono-, di- and tri-ethanol ammonium cations, or combinations thereof, are the most suitable for purposes of this invention. In general, sodium soaps are used in the compositions of this invention, but from about 1% to about 25% of the soap may be potassium, magnesium or triethanolamine soaps. The soaps useful herein are the well known alkali metal salts of natural or synthetic aliphatic (alkanoic or alkenoic) acids having about 8 to about 22 carbon atoms, preferably about 10 to about 18 carbon atoms. They may be described as alkali metal carboxylates of saturated or unsaturated hydrocarbons having about 8 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are $C_{16}$ and higher. Preferred soap for use in the compositions of this invention has at least about 85% fatty acids having about 12 to 18 carbon atoms.

Coconut oil employed for the soap may be substituted in whole or in part by other "high-lauric" or "lauric rich" oils, that is, oils or fats wherein at least 50% of the total fatty acids are composed of lauric or myristic acids and mixtures thereof. These oils are generally exemplified A preferred soap is a mixture of about 10% to about 40% derived from coconut oil, palm kernel oil or other lauric rich oils ("lauric-rich soaps") and about 90% to about 60% tallow, palm oil or other stearic rich oils ("stearic-rich soaps").

The soaps may contain unsaturation in accordance with commercially acceptable standards. Excessive unsaturation is normally avoided because of the potential for rancidity.

Soaps may be made by the classic kettle boiling process or modern continuous soap manufacturing processes wherein natural fats and oils such as tallow, palm oil or coconut oil or their equivalents are saponified with an alkali metal hydroxide using procedures well known to those skilled in the art. Two broad processes are of particular commercial importance. The SAGE process where triglycerides are saponified with a base, e.g., sodium hydroxide and the reaction products extensively treated and the glycerin component extracted and recovered. The second process is the SWING process where the saponification product is directly used with less exhaustive treatment and the glycerin from the triglyceride is not separated but rather included in the finished soap noodles and/or bars.

Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

The level of fatty acid soap in the bar (generally a mixture of different chain lengths and/or isomers) can range from 40% to less than 60%, preferably 45% to less than 60%, more preferably 45% to 55% and most preferably 45% to 52% based on the total weight of the bar composition.

Surfactants other than soap (commonly known as "synthetic surfactants" or "syndets") can optionally be included in the bar at levels up to about 25%, preferably up to 15%, more preferably 2% to 10% and most preferably 2% to 7% by weight of the bar. Examples of suitable syndets are described below under OPTIONAL INGREDIENTS.

Added Soluble Salts

By the term "added" soluble salt is meant one or more salts that are introduced in the bar in addition to the salts which are presenting the bar as a result of saponification and neutralization of the fatty acids, e.g., NaCl generated from saponification with sodium hydroxide and neutralization with hydrochloric acid.

A variety of water soluble salts could potentially be used. The preferred salts are water soluble salts that do not contain cations which precipitate with soap, i.e., which form insoluble precipitates with fatty acid carboxylates. Thus, water soluble salts containing divalent ions such as calcium magnesium and zinc and trivalent ions such as aluminum should be avoided. Of course highly insoluble calcium salts such as calcium carbonate may be used as optional insoluble particles as part of the structuring system (see below).

Especially preferred soluble salts comprise monovalent cations that form soluble fatty acid soaps (such as sodium, potassium, alkylanoammonium but no lithium) and divalent anions (e.g., sulfates, carbonates, and isethionates), trivalent anions (e.g., citrates, sulfosuccinates, phosphates) and multivalent anions (e.g., polyphosphates and polyacylates).

Especially preferred salts are sodium and potassium sulfates, carbonates, phosphates, citrates, sulfosuccinates and isethionates and mixtures thereof.

Without wishing to be bound by theory, it is believed that a limited amount of the one or more water soluble salts reduces the level of liquid crystal phase (e.g., lamellar phase) in the bar and therefore allow the bar to accommodate a composite structuring system that itself comprises some liquid. However, the incorporation of too much salt reduces the liquid crystal phase to a level where the bar becomes insufficiently pliable and exhibits excessive cracking.

The level of salt should be at least about 0.3% but less than 2.0, preferably 0.3% to less than 1.50%, more preferably 0.3% to 0.80%.

It should be noted that the role of salts in the current invention is not primarily a lowering of water activity so as to accommodate very high levels of water in the bar which are characteristic of low TFM bars described in the prior art, i.e. the use of electrolytes to prevent or slow the drying out of the bar. In fact, the bars of the current invention have water levels that are not especially high (up to about 20%) compared with normal commercial soap bars which can range from about 13 to about 15-18%. Thus, levels of salts in the range of 2.5 to 8% typical of the high water content bars of the prior art would be detrimental to the bars described herein.

Fatty Acid

A useful optional ingredient is fatty acid. Although it is well know that fatty acids are useful in improving lather, their primary function in bars described herein is modify rheology at low levels incorporated in the bar composition so as to provide adequate thermo-plasticity to the mass.

Potentially suitable fatty acids are $C_8$-$C_{22}$ fatty acids. Preferred fatty acids are $C_{12}$-$C_{18}$, preferably predominantly saturated, straight-chain fatty acids. However, some unsaturated fatty acids can also be employed. Of course the free fatty acids can be mixtures of shorter chain length (e.g., $C_{10}$-$C_{14}$) and longer chain length (e.g., $C_{16}$-$C_{18}$) chain fatty acids. For example, one useful fatty acid is fatty acid derived from high-lauric triglycerides such as coconut oil, palm kernel oil, and babasu oil.

The fatty acid can be incorporated directly or they can be generated in-situ by the addition of a protic acid to the soap during processing. Examples of suitable protic acids include: mineral acids such as hydrochloric acid and sulfuric acid, adipic acid, citric acid, glycolic acid, acetic acid, formic acid, fumaric acid, lactic acid, malic acid, maleic acid, succinic acid, tartaric acid and polyacrylic acid.

The level of fatty acid should not exceed 5.0%, preferably not exceed about 1% and most preferably be between 0.3% and 0.8% based on the total weight of the bar composition.

Structuring System

The structuring system includes one or more starch components, one or more polyols and optionally, water insoluble particles (i.e., particulate material).

The total level of the structuring system used in the bar composition can be at from about 20% but less than 60%, preferably from 25% to less than 60% based on the total weight of the bar composition. By total level of the structuring system is meant the sum of the weights of the starch, polyol, and optional insoluble particle components.

Suitable starch materials include natural starch (from corn, wheat, rice, potato, tapioca and the like), pregelatinized starch, various physically and chemically modified starch and mixtures thereof. By the term natural starch is meant starch which has not been subject to chemical or physical modification—also known as raw or native starch.

A preferred starch is natural or native starch from maize (corn), cassava, wheat, potato, rice and other natural sources of it. Raw starch with different ratio of amylase and amylopectic: e.g. maize (25% amylase); waxy maize (0%); high amylase maize (70%); potato (23%); rice (16%); sago (27%); cassava (18%); wheat (30%) and others. The raw starch can be used directly or modified during the process of making the bar composition such that the starch becomes gelatinized, either partially or fully gelantinized.

Another suitable starch is pre-gelatinized which is starch that has been gelatinized before it is added as an ingredient in the present bar compositions. Various forms are available that will gel at different temperatures, e.g., cold water dispersible starch. One suitable commercial pre-gelatinized starch is supplied by National Starch Co. (Brazil) under the trade name FARMAL CS 3400 but other commercially available materials having similar characteristics are suitable.

The amount of the starch component in the filler can range from about 5% to about 30%, preferably 6% to 25%, preferably 10% to 25%, preferably 10% to 20%, and preferably 10% to 15% by weight of total bar composition.

A second critical component of the structuring system is a polyol or mixture of polyols. Polyol is a term used herein to designate a compound having multiple hydroxyl groups (at least two, preferably at least three) which is highly water soluble, preferably freely soluble, in water.

Many types of polyols are available including: relatively low molecular weight short chain polyhydroxy compounds such as glycerol and propylene glycol; sugars such as sorbitol, manitol, sucrose and glucose; modified carbohydrates such as hydrolyzed starch, dextrin and maltodextrin, and polymeric synthetic polyols such as polyalkylene glycols, for example polyoxyethylene glycol (PEG) and polyoxypropylene glycol (PPG).

Preferred polyols are relatively low molecular weight compound which are either liquid or readily form stable highly concentrated aqueous solutions, e.g., greater than 50% and preferably 70% or greater by weight in water. These include low molecular weight polyols and sugars.

Especially preferred polyol are glycerol, sorbitol and their mixtures.

The level of polyol is critical in forming a thermoplastic mass whose material properties are suitable for both high speed manufacture (300-400 bars per minute) and for use as a personal washing bar. It has been found that when the polyol level is too low, the mass is not sufficiently plastic at the extrusion temperature (e.g., 40° C. to 45° C.) and the bars tend to exhibit higher mushing and rates of wear. Conversely, when the polyol level is too high, the mass becomes too soft to be formed into bars by high speed at normal process temperature.

The level of polyol should be between 5.0% and 30.0%, preferably 6 to 25% and preferably about 8% to about 20% by weight based on the total weight of the bar composition. Furthermore, it has been found that the ratio of polyols to starch be preferably between about 1:1 to 1:4.5 by weight, and more preferably between 1:1 and 1:1.25.

As indicated above, it is unexpected and unpredictable that high polyol levels would lead to enhanced perfume retention during storage. Apparently and while not wishing to be bound by theory, however, these higher polyol levels “suppress” perfume and, because of this suppression, less perfume was lost to the vapor phase during storage (e.g., higher concentration is maintained and has more olfactory impact).

The structuring system may optionally include insoluble particles comprising one or a combination of materials. By insoluble particles is meant materials that are present in solid particulate form and suitable for personal washing. The particulate material can potentially be inorganic or organic or a combination as long as it is insoluble in water. The insoluble particles should not be perceived as scratchy or granular and thus should have a particle size less than 300 microns, more preferably less than 100 microns and most preferably less than 50 microns.

Preferred inorganic particulate material includes talc and calcium carbonate. Talc is a magnesium silicate mineral material, with a sheet silicate structure and a composition of $Mg_3Si_4(OH)_{22}$, and may be available in the hydrated form. It has a plate-like morphology, and is essentially oleophilic/hydrophobic, i.e., it is wetted by oil rather than water.

Calcium carbonate or chalk exists in three crystal forms: calcite, aragonite and vaterite. The natural morphology of calicite is rhombohedral or cuboidal, acicular or dendritic for aragonite and spheroidal for vaterite.

Commercially, calcium carbonate or chalk known as precipitated calcium carbonate is produced by a carbonation method in which carbon dioxide gas is bubbled through an aqueous suspension of calcium hydroxide. In this process the crystal type of calcium carbonate is calcite or a mixture of calcite and aragonite.

Examples of other optional insoluble inorganic particulate materials include alumino silicates, aluminates, silicates, phosphates, insoluble sulfates, borates and clays (e.g., kaolin, china clay) and their combinations.

Organic particulate materials include: insoluble polysaccharides such as highly cross linked or insolubilized starch (e.g., by reaction with a hydrophobe such as octyl succinate) and cellulose; synthetic polymers such as various polymer lattices and suspension polymers; insoluble soaps and mixtures thereof.

The structuring system can comprise up to 10% insoluble particles, preferably 5% to 8%, based on the total weight of the bar composition.

Water Content

As already mentioned the bar compositions of the invention do not comprise an especially high level of water compared to typical extruded and stamped soap bars which typically can range from about 13 to about 18% water when freshly made, i.e., after extrusion and stamping. In fact, it is preferably that the water content of the freshly made bar should be less than 20% and preferably be between 14% and 18% based on the total weight of the bar. Thus, in preferred embodiments, the water level of the freshly made bars of the invention is lower than the water content of freshly made melt and pours or melt-cast bars, i.e., the nominal water content based on the formulation, which typically exceeds 25% by weight in melt-cast compositions.

It is stressed that the preferred water levels quoted above refers to freshly made bars. As is well known, soap bars are subject to drying out, i.e., water evaporation. Hence depending upon how the bar is stored (type of wrapper, temperature, humidity, air circulation, etc.) the actual water content of the bar at the moment of sampling can obviously differ significantly from the initial water content of the bar immediately after manufacture.

Optional Ingredients

Synthetic Surfactants:

The bar compositions can optionally include non-soap synthetic type surfactants (detergents)—so called syndets. Syndets can include anionic surfactants, nonionic surfactants, amphoteric or zwitterionic surfactants and cationic surfactants.

The level of synthetic surfactant present in the bar is generally less than 25%, preferably less than 15%, preferably up to 10%, and most preferably from 0 to 7% based on the total weight of the bar composition.

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl either sulfonate (AGS); or an aromatic sulfonate such as alkyl benzene sulfonate. Alpha olefin sulfonates are another suitable anionic surfactant.

The anionic may also be an alkyl sulfate (e.g., $C_{12}$-$C_{18}$ alkyl sulfate), especially a primary alcohol sulfate or an alkyl ether sulfate (including alkyl glyceryl ether sulfates).

The anionic surfactant can also be a sulfonated fatty acid such as alpha sulfonated tallow fatty acid, a sulfonated fatty acid ester such as alpha sulfonated methyl tallowate or mixtures thereof.

The anionic surfactant may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates or lactylates, $C_8$-$C_{22}$ monoalkyl succinates and maleates, sulphoacetates, and acyl isethionates.

Another class of anionics is $C_8$-$C_{20}$ alkyl ethoxy (1-20 EO) carboxylates.

Another suitable anionic surfactant is $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have form 6 to 10 carbon atoms. The acyl isethionate may also be alkoxylated isethionates.

Acyl isethionates, when present, will generally range from about 0.5% to about 25% by weight of the total composition.

In general, the anionic component will comprise the majority of the synthetic surfactants used in the bar composition.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. Suitable amphoteric surfactants include amphoacetates, alkyl and alkyl amido betaines, and alkyl and alkyl amido sulphobetaines.

Amphoacetates and diamphoacetates are also intended to be covered in possible zwitterionic and/or amphoteric compounds which may be used.

Suitable nonionic surfactants include the reaction products of compounds having a hydrophobic group and a reactive hydrogen atom, for example aliphatic alcohols or fatty acids, with alkylene oxides, especially ethylene oxide either alone or with propylene oxide. Examples include the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as alkyl polysaccharides and alkyl polysaccharide amides.

Examples of cationic detergents are the quaternary ammonium compounds such as alkyldimethylammonium halides.

Other surfactants which may be used are described in U.S. Pat. No. 3,723,325 to Parran Jr. and "Surface Active Agents and Detergents" (Vol. I & II) by Schwartz, Perry & Berch, both of which is also incorporated into the subject application by reference.

Slip Modifier:

Very useful optional ingredients are slip modifiers. The term "slip modifier" is used herein to designate materials that when present at relatively low levels (generally less than 1.5% based on the total weight of the bar composition) will significantly reduce the perceived friction between the wet bar and the skin. The most suitable slip modifiers are useful at a level of 1% or less, preferably from 0.05 to 1% and more preferably from 0.05% to 0.5%.

Slip modifiers are particularly useful in bar compositions which contain starch and/or insoluble particles whose levels approach the higher end of the useful concentration range for these materials, e.g., 20-25% for starch. It has been found that the incorporation of higher levels of starch and/or insoluble particles increases the wet skin friction of the bar and the bars are perceived as "draggy" (have a high perceived level of frictional "drag" on the skin). Although some consumers do not mind this sensory quality, others dislike it. In general, consumers prefer bars that are perceived to glide easily over their skin and are perceived as being slippery.

It has been found that certain hydrophobic materials can at low levels dramatically reduce the wet skin frictional drag of bars containing higher levels of starch and/or insoluble particles. This greatly improves consumer acceptability of such bars.

Suitable slip modifiers include petrolatum, waxes, lanolines, poly-alkane, -alkene, -polalkyalyene oxides, high molecular weight polyethylene oxide resins, silicones, poly ethylene glycols and mixtures thereof.

Particularly suitable slip modifiers are high molecular weight polyethylene oxide resins because they have been found to be effective at relatively low concentrations in the composition. Preferably the molecular weight of the polyethylene oxide resin is greater than 80,000, more preferably at least 100,000 Daltons and most preferably at least 400,000 Daltons. Examples of suitable high molecular weight polyethylene oxide resins are water soluble resins supplied by Dow Chemical Company under the grade name POLYOX. An example is WSR N-301 (molecular weight 4,000,000 Daltons).

Adjuvants:

Adjuvants are ingredients that improve the aesthetic qualities of the bar especially the visual, tactile and olefactory properties either directly (perfume) or indirectly (preservatives). A wide variety of optional ingredients can be incorporated in the bar composition of the invention. Examples of adjuvants include but are not limited to perfumes; opacifying agent such as fatty alcohols, ethoxylated fatty acids, solid esters, and $TiO_2$; dyes and pigments; pearlizing agent such as $TiO_2$ coated micas and other interference pigments; plate like mirror particles such as organic glitters; sensates such as menthol and ginger; preservatives such as dimethyloldimethylhydantoin (Glydant XL1000), parabens, sorbic acid and the like; antioxidants such as, for example, butylated hydroxytoluene (BHT); chelating agents such as salts of ethylene diamine tetra acetic acid (EDTA) and trisodium etridronate; emulsion stabilizers; auxiliary thickeners; buffering agents; and mixtures thereof.

The level of pearlizing agent should be between about 0.1% to about 3%, preferably between 0.1% and 0.5% and most preferably between about 0.2 to about 0.4% based on the total weight of the bar composition.

Skin Benefit Agents:

A particular class of optional ingredients highlighted here is skin benefit agents included to promote skin and hair health and condition. Potential benefit agents include but are not limited to lipids such as cholesterol, ceramides, and pseudoceramides; antimicrobial agents such as TRICLOSAN; sunscreens such as cinnamates; other types of exfoliant particles such as polyethylene beads, walnut shells, apricot seeds, flower petals and seeds, and inorganics such as silica, and pumice; additional emollients (skin softening agents) such as long chain alcohols and waxes like lanolin; additional moisturizers; skin-toning agents; skin nutrients such as vitamins like Vitamin C, D and E and essential oils like bergamot, *citrus unshiu*, calamus, and the like; water soluble or insoluble extracts of avocado, grape, grape seed, myrrh, cucumber, watercress, *calendula*, elder flower, geranium, linden blossom, amaranth, seaweed, gingko, ginseng, carrot; *impatiens balsamina*, camu camu, alpine leaf and other plant extracts such as witch-hazel, and mixtures thereof.

The composition can also include a variety of other active ingredients that provide additional skin (including scalp) benefits. Examples include anti-acne agents such as salicylic and resorcinol; sulfur-containing D and L amino acids and their derivatives and salts, particularly their N-acetyl derivatives; anti-wrinkle, anti-skin atrophy and skin-repair actives such as vitamins (e.g., A, E and K), vitamin alkyl esters, minerals, magnesium, calcium, copper, zinc and other metallic components; retinoic acid and esters and derivatives such as retinal and retinol, vitamin B3 compounds, alpha hydroxyl acids, beta hydroxyl acids, e.g. salicylic acid and derivatives thereof; skin soothing agents such as aloe vera, jojobe oil, propionic and acetic acid derivatives, fenamic acid derivatives; artificial tanning agent such as dihydroxyacetone; tyrosine; tyrosine esters such as ethyl tyrosinate and glucose tyrosinate; skin lightening agents such as aloe extract and niacinamide, alpha-glyceryl-L-ascorbic acid, aminotyroxine, ammonium lactate, glycolic acid, hydroquinone, 4 hydroxyanisole, sebum stimulation agents such as bryonolic acid, dehydroepiandrosterone (DHEA) and orizano; sebum inhibitors such as aluminum hydroxyl chloride, corticosteroids, dehydroacetic acid and its salts, dichlorophenyl imidazoldioxolan (available from Elubiol); anti-oxidant effects, protease inhibition; skin tightening agents such as terpolymers of vinylpyrrolidone, (meth)acrylic acid and a hydrophobic monomer comprised of long chain alkyl (meth)acrylates; anti-itch agents such as hydrocortisone, methdilizine and trimeprazine hair growth inhibition; 5-alpha reductase inhibitors; agents that enhance desquamation; anti-glycation agents; anti-dandruff agents such as zinc pyridinethione; hair growth promoters such as finasteride, minoxidil, vitamin D analogues and retinoic acid and mixtures thereof.

With regard to perfumes which may be used, perfume may be used for purposes of the invention although perfumes which are less volatile are preferred.

Perfumes may be classified into four categories according to oil/water partition coefficients and volatility constants as described, for example, in U.S. Pat. No. 6,806,249 to Yang et al., hereby incorporated by reference in its entirety, into the subject application.

For example, fragrance molecules in Type 1 category have low partition coefficient (reflection of low solubility in surfactant phase) and high volatility and Type 2 molecules have high partition coefficient and low volatility (e.g., they readily dissolve in surfactant, but are not very volatile). Specific examples of Type 2 perfume molecules include allyl cyclohexane propionate, amyl benzoate, amyl cinnamate and other molecules noted, for example, in U.S. Pat. No. 6,806,249 at column 7, lines 9-37.

Volatility constant (K) is a constant that describes the relation between the perfume concentration (x) in a continuous phase (e.g., water phase of a surfactant water solution) and the perfume partial pressure in the vapor phase (Pi):

$$P_i=Kx$$

K can be determined experimentally and typically is in the unit of atmosphere (atm). The higher the K value, the higher the volatility of the perfume compounds from the solution of interest to the vapor phase.

Typically, volatile perfumes have volatility constant of about 2 to 1000, especially 50 to 1000 atmospheres and "low volatility" molecules have volatility constant below 2, preferably 1.5 and below, more preferably about 1 atmosphere and lower.

Type 3 molecules typically have high oil/water partition coefficient and high volatility; typical examples include allyl caproate, anisole, camphene, citral and other molecules note at column 7, lines 49-65 of U.S. Pat. No. 6,806,249.

Type 4 perfume molecules have low oil/water partition coefficient and low volatility. Typical molecule include benzyl acetate, benzyl acetone, cinnamyl acetate and molecules noted at column 8, lines 17-37 of U.S. Pat. No. 6,806,249 B2.

As discussed in examples, although all perfumes can be used, it was noted that lower volatility perfumes are preferred.

Material Properties of an Extruded Mass

The personal washing bars used in the method of the invention and described herein are extruded masses. By the term "extruded masses" is meant that the bars are made by a process which involved both the intensive mixing and working of the soap mass while it is in a semi-solid plastic state and it's forming into a cohesive mass by the process of extrusion.

The intensive mixing can be accomplished by one or more unit operations known in the art which can include roller milling, refining, and single or multistage extrusion. Such processes work the bar mass, e.g., soap mass, at a temperature between about 30° C. and about 50° C. to form a homogeneous network of insoluble materials in a viscous liquid and/or liquid crystalline phase containing the lower melting, more soluble surfactants (e.g., soaps and other water soluble/dispersible materials).

An extruded mass must be thermoplastic within the process temperature of extrusion which is generally between about 30° C. and about 45° C., preferably at a temperature between about 33° C. to about 42° C. Thus, the material must soften within this process temperature window but remain highly viscous, i.e., not softer excessively to form a sticky mass. The material must regain its structure and harden quickly as the temperature is lowered below its softening point. This means that the internal structure must reform quickly generally by re-solidification of structure forming units, e.g., crystals.

Furthermore, the softened mass although pliable must be sufficiently viscous so that it does not stick to the surfaces of the extruder in order to be capable of conveyance by the extruder screws but not bend excessively when exiting the extruder as a billet. However, if the mass is too viscous it will not be capable of extrusion at reasonable rates. Thus, the hardness of the mass should fall within limits within the process temperature window to be capable of high rates of production. By high rate of production is meant in excess of about 50 tablet or bars per minute (4.5 Kg/min for a 90 Kg bar), preferably greater than about 150 bars per minute (13.5 Kg/min), more preferably greater than 250 bars per minute (22.5 Kg/min) and still more preferably greater than 400 bars per minute (36 Kg/min).

Personal washing bars formed by extrusion (also commonly known as milled soaps) have physical-chemical properties and an internal structure which are quite different from soaps that are made by a melt-cast process wherein the bar composition is first melted at high temperature (e.g., 70° C.) to form a liquid phase which is then poured into molds to solidify by quiescent cooling.

These differences in internal structure, composition and physical-chemical characteristics provide extruded personal washing bars with overall in-use properties which are better suited for the mass market than cast soaps. These properties include: much lower wear rates, more resistance to scuffing and denting, and a richer, more creamy opaque lather.

The one or more key properties that serve as characteristic "finger-prints" of an extruded mass are structural anisotropy, the level of high melting point materials such as stearic soaps, high melting point and thermal reversibility, and rapid recovery of hardness after heating and shear. These characteristics are briefly described below.

Structural Anisotropy

Bars made by extrusion typically have a characteristic anisotropic internal structure both with respect to the alignment of crystals and overall macro-structure.

One important element of the macro-structure is the "candle structure", disclosed for example by Schonig et al. in U.S. Pat. No. 4,720,365 which is produced in the plodder and modified in the stamper. Shear forces generated at the eye-plate and subsequent extensional forces in the plodder cone produce marked alignment within the candles and thus influence the colloidal structure of the extruded mass. Although there is some modification of alignment after stamping, the resultant bar usually has a characteristic macroscopic alignment of the crystallites and domains relative to the bar surface and some residual candle structure.

The liquid (crystalline) phase generated at the extrusion temperature has a relatively lower viscosity and is expected to preferentially flow to the surface of the candles during the plodder compression stage.

In contrast, melt-case bars have a predominantly isotropic structure because crystallization occurs during quiescent cooling and thus the alignment of crystals is minimal and there is no candle structure.

The differences in internal structure between extruded and melt-case bars can be visualized by a simple ethanol extraction procedure. In this procedure bars are shaven, for example with a plane of mandolin to reveal inside surfaces (the bars can be shaved in several orthogonal directions). These shaved sections are then immersed overnight in anhydrous alcohol. After removal from the alcohol, the bars are allowed to dry by standing a pattern of small cracks appears. These cracks are indicative of the oriented micro-structure of the bar. The alcohol extracts the more soluble soaps in extruded bars, thus exposing the candle structure interface and the lines of flow. In melt-cast bars flow lines and the candle structure are absent and fine cracks are much less pronounced or absent after alcohol emersion.

Level of High Melting Materials

In order to achieve the rheological properties required for milling and extrusion, an extruded mass must have a sufficient level of solid particles to adequately structure the mass at the process temperature, i.e., the bar contains materials whose melting point is above the extrusion temperature.

For bars that are comprised predominantly of soap, these high melting solids are provided in at least part by the stearic soaps which include the C16 and C18 saturated soaps.

The level of high melting solids (melting point greater than the extrusion temperature) found in extruded bars is generally greater than 20%, and typically greater than 30%. For an extruded bar suitable for the instant invention which are predominantly comprised of soaps, the level of stearic-rich soaps is generally between about 25% and about 55% based on the total weight of bar, preferably between 25% to about 40%. Other sources of solid particles are also present in the bars described herein.

Melting Point and Thermal Reversibility

Because of the presence of significant high melting solids (e.g. steric-rich soaps and structurants) and the lower levels of liquids relative to cast soaps, extruded masses have melting points that are generally above 80° C., typically above 90° C. and usually above 100° C. In contrast, cast soaps generally melt at temperature between 70° C. and 80° C.

Furthermore an extruded mass regains its structure and hardens quickly as the temperature is lowered below its softening point. This means that the internal structure reform quickly, generally by re-solidification of structure forming units, e.g., soap crystals. This rapid re-solidification is generally observed as thermal reversibility in differential scanning calorimetry (DSC). By the term thermal reversibility is meant that increasing and decreasing temperature sweeps tend to be super imposable albeit offset by a temperature difference characteristic of the composition. In contrast, cast soaps require much longer periods of time to reform the solid structural units and exhibit lower thermal reversibility, e.g., increasing-decreasing temperature sweeps are either not super-impossible or are offset by much larger temperatures than is found with an extruded mass.

Recovery of Hardness after Heating and Shear

An extruded mass must soften when it is heated to the extrusion process temperature which is typically in the range of about 35° C. to about 45° C. However, at this temperature it must retain sufficient hardness. It has been found experimentally that to achieve the desired rates of production, the hardness of the mass should generally be at least about 1500 g, preferably at least 3000 g but generally not greater than about 8000 g, preferably between 3000 g and 5000 g when measured by the Hardness Penetration Test described in the TEST METHODOLOGY section, said measurement being carried out at a temperature in the range of about 40° C.

An extruded mass also remains cohesive after it has been subjected to sheer at the extrusion temperature without exhibiting excessive pliability or stickiness. By the term "remain cohesive" is meant when compacted under pressure the mass should be capable of sintering together to form a single cohesive unit that has mechanical integrity.

Finally, it has been found that an extruded mass quickly recovers its yield stress (as measured by its penetrometer hardness) when it is subjected to shear at the extrusion temperature (e.g., 40° C.) and allowed to cool. For example when the extrudate is cooled after extrusion to 25° C., the mass should recover at least about 75%, preferably at least about 85% and more preferably at least about 95% of the initial hardness before it was sheared, by for example, extrusion through an "orifice" extruder—see below.

The influence of shear on cohesivity, stickiness, pliability and recovery of yield stress can be assessed utilizing an "orifice" extruder which provides a controlled extensional flow similar to that encountered by the mass during extrusion through an eye plate. This device comprises a thermal jacketed barrel (e.g., 350 mm length by 90 mm in diameter) ending in a narrow opening (typically 2-4 mm) and a plunger which is coupled to a drive unit e.g., Instron Mechanical Tester. The plunger forces the mass through the orifice to form an extrudate. The extrudate can be assessed at the process temperature.

The extrudate can be placed in the barrel of the orifice extruder, compressed under different loads and removed to determine its cohesivity or extent of cohesion, I its stickiness and its ability to recover its hardness after it has been sheared at the extrusion temperature (e.g., 40° C.) and cooled (e.g., 25° C.).

Based on the above extrudability criteria, so called melt and pour compositions such as those used to make glycerin soaps that require casting in molds in order to form bars are not extrudable masses when they are initially formed from the melt and are not suitable. Thus, after a cast melt composition is melted and allowed to solidify in a mold for several hours, the composition does not form a cohesive non-sticky mass after extrusion through an orifice extruder and the extrudate does not exhibit the required recovery of hardness after cooling.

In addition to the requirement of being suitable for extrusion, the bar mass should also be sufficiently hard to be stamped with conventional soap making dies. The stamping process involves placing a billet or ingot of the extruded mass into a split mold comprised of generally two moveable halves (the dies). These dies when closed compress the billet ("stamp" the billet), squeezing out excess mass and defining the ultimate shape of the bar. The mold halves meet at a parting line which becomes visible as a line on the edge perimeter of the molded finished bar (stamped bar). Thus, a stamped personal washing bar can be characterized as comprising top and bottom stamped faces meeting at a parting line.

Experience has shown that stamping can be achieved by ensuring that an extruded billet of the bar mass (also known as an ingot) has a minimum hardness of at least about 1500 g at the stamping temperature which is typically in the range 25° C. to 45° C.

The one or more key characteristics of an extruded mass are summarized in the table below.

| CHARACTERISTIC PROPERTY | EXTRUDED MASS | CAST SOAP |
|---|---|---|
| Structural anisotropy | Aligned crystals<br>Distinct flow lines/candle structure evident as small cracks formed after alcohol emersion | Generally random crystal orientation<br>Absence of candle structure<br>No prominent and systematic lines or cracks evident after alcohol emersion |

-continued

| CHARACTERISTIC PROPERTY | EXTRUDED MASS | CAST SOAP |
|---|---|---|
| Levels of stearic-rich soaps $C_{16}/C_{18}$ soaps) | 20% to about 55% based on the total weight of bar | Generally less than 15% or absent |
| Melting point/Thermal characteristics | Melting point above 80° C., typically above 90° C. and usually above 100° C. Relatively high degree of thermal reversibility (DSC) | Melting point 70° C. and 80° C. Relatively low degree of thermal reversibility |
| Recovery of hardness After heating and shear | Recovers at least about 75%, preferably at least about 85% and more preferably at least about 95% of its initial hardness before shearing. Forms cohesive mass after extensional shear (Orifice extruder) | After melting and casting either low recovery of hardness after shear and/or lack of formation of cohesive mass after shear (excessive fracture or softening) |

In addition, the various test methodologies required to test bars for hardness, wear rate, bar mush, cracking, etc. (i.e., to determine whether extruded or not) are well known to those skilled in the art. Such tests are described, for example, in Great Britain Application No. 0806340.6 to Leopoldino et al. or GB 0901953.0 to Canto et al., both of which are incorporated by reference into the subject application.

EXAMPLES

Examples 1-6

Formulations: In order to study perfume retention effect during storage, compositions listed in Table 1 below were prepared. Compositions of examples 1 and 2 have much lower TFM level compared to a conventional bar (~80% in conventional bars vs. ~50% in these examples). In these examples, starch, glycerine, talc and sorbitol were or could be used to replace the lowered TFM. Soap bars with higher TFM values (Control Examples A and B) were used as controls.

TABLE 1

Formulation Information

| Formulations Ingredients (%) | Example 1 Bar prototype A (SL 50 Sorbitol) | Example 2 Bar prototype B (SL 50 Gly) | Control A | Control B |
|---|---|---|---|---|
| Anhydrous 80/20 sodium soap | 52 | 52 | — | — |
| Anhydrous 90/10 sodium soap | — | — | 84.5 | 74.5 |
| Starch | 14 | 14 | — | — |
| Sorbitol | 6 | — | — | — |
| Glycerol | — | 6 | — | — |
| Talc | — | — | — | — |
| Calcium Carbonate (ppt) | 10 | 10 | — | 10 |
| Water | 16 | 16 | 13.5 | 13.5 |
| Minor ingredients | 2 | 2 | 2 | 2 |
| TFM | 48 | 48 | 78.8 | 68.8 |
| Fatty matter origin | Tallow/ PKO | Tallow/ PKO | Tallow/ PKO | Tallow/ PKO |

TFM = total fatty matter
PKO = palm kernel oil

Fragrance oil composition: Two commercially available perfume oils were chosen to study perfume retention in the low TFM bars (Examples 1 and 2) noted in Table 1 above. Their compositions in terms of top notes (compounds with high volatilities), middle notes (compounds with intermediate volatilities) and bottom notes (compounds with least volatilities), as well as solvent (dipropylene glycol), are listed in Table 2 below. Perfume 1 is a representative of perfume oils with relatively high overall volatilities. Perfume 2 is a representative of perfume oils that are well balanced in terms of top, middle and bottom notes.

TABLE 2

Solvent/top/middle/bottom content in Perfume 1 and 2 perfume oils

| | Perfume 1 | Perfume 2 |
|---|---|---|
| Solvent | 7 | — |
| Top notes | 55 | 36.9 |
| Middle notes | 18 | 22.1 |
| Bottom notes | 27 | 40.7 |

Applicants ran one set of tests in which they tested percentage of perfume 1 retained (total perfume headspace FID (flame ionization detector) peak area over bar surface) after one month storage at 50° C., normalized to the total perfume headspace FID peak area over bar surface at time zero. A higher FID area is correlated to higher perfume concentration in the vapor phase, e.g., perfume retained in bar after storage at 50° C., and thus higher olfactory impact after storage. A second identical set of tests were run for perfume 2. Results of both sets of tests are set forth in Tables 3 and 4 below.

TABLE 3

Perfume 1

| Example | Bar composition | Percentage of perfume retaining after 1 month 50° C. storage compared to time zero |
|---|---|---|
| Example 3 | Bar prototype A | 22 ± 2% |
| Example 4 | Bar prototype B | 22 ± 2% |
| Control 1.A | Control A | 14 ± 1.4% |
| Control 1.B | Control B | 11 ± 1.1% |

TABLE 4

| Perfume 2 | | |
|---|---|---|
| Example | Bar composition | Percentage of perfume retaining after 1 month 50° C. storage compared to time zero |
| Example 5 | Bar prototype A | 76 ± 7.6% |
| Example 6 | Bar prototype B | 100 ± 10% |
| Control 2.A | Control A | 145± 4.5% |
| Control 2.B | Control B | 50 ± 5% |

As clearly seen, there is a strong advantage (higher retention) using either perfume 1 (Table 3) or 2 (Table 4) with bar formulations of Examples 1 or 2 (structured with starch and sorbitol or glycerol) versus use of the same perfume in control A or B (higher TFM) bars. While overall headspace varies depending on specific perfume used (and there is no limitation as to what perfume may be used although less volatile perfumes are preferred), the overall feel is the same, i.e., the headspace (a function of retention) after 1 month storage at 50° C. is higher over the bar prototype A and bar prototype B (example 1 and 2) compared to that over control bars. This result indicates that less perfume is lost into vapor phase in the polyol starch structured bar systems of the invention.

Examples 7-10

Applicants prepared the same formulations as set forth in Table 1 to run a second set of experiments (set forth in Tables 5 and 6 below). In these tests, applicants measured FID peak area over base surface after the bars had been washed twice a day and stored at ambient temperature for 20 days and reached about two thirds (⅔) of original bar weight (e.g., bar weight losses due to wash). Measurement was normalized to time zero. Again, applicants ran the test for both perfume 1 and perfume 2 and results are set forth in Tables 5 and 6 below:

TABLE 5

| Perfume 1 | | |
|---|---|---|
| Example | Bar Composition | Percentage of perfume retaining after wash to 2/3 of bar weight |
| Example 7 | Bar prototype A | 39 ± 3.9% |
| Example 8 | Bar Prototype B | 37 ± 3.7% |
| Control 3.A | Control A | 47 ± 4.7% |
| Control 3.B | Control B | 45 ± 4.5% |

TABLE 6

| Perfume 2 | | |
|---|---|---|
| Example | Bar composition | Percentage of perfume retaining after wash to 2/3 of bar weight |
| Example 9 | Bar prototype A | 71 ± 7.1% |
| Example 10 | Bar prototype B | 68 ± 6.8% |
| Control 4.A | Control A | 79 ± 7.9% |
| Control 4.B | Control B | 62 ± 6.2% |

As discussed in Results section in these examples (in contrast to Examples 3-6, Table 3 and Table 4), there is little or no difference in perfume retention under twice a day wash/store in ambient temperature condition as illustrated in Table 5 and Table 6.

Methodology of Examples

Experimental method for measurement of fragrance loss during storage and prior to use: The freshly made bars were first stored at room temperature for about 10 days to equilibrate. The bars were then stored in a 50° C. storage oven for one month. Then the bars were shaved from the surface (around 0.5 cm deep) to collect bar flake samples for gas chromatography (GC) analysis which represent the perfume impact from the bar surface.

Experimental method for measurement of fragrance loss for bars after use: The freshly made bars were first stored at room temperature for about 10 days to equilibrate. The soap bars were then washed twice a day under running water (water temperature around 75 F). The bars were rotated 30 times with gloved hands. The washes were conducted by one person. After each wash, the soap bars were patted dry with a paper towel and placed on a wire rack at room temperature. Washed soap bars were sampled from the bar surface when the bar weight reached ⅓ of the original total bar weight.

For both fragrance loss tests, GC samples (2 g of bar flakes were weighed into 20 ml GC vials) were left at room temperature for at least 12 hours before GC measurement to ensure equilibrium of perfume in headspace. There was no incubation (all experiments were done at room temperature) on autosampler for these samples. The details of the GC conditions are set forth below.

| 6890 GC METHOD | | | |
|---|---|---|---|
| OVEN | | | |
| Initial temp: 75° C. (On) | | Initial time: 2.00 min. | |
| Ramps: | | | |
| # | Rate | Final temp | Final time |
| 1 | 15.00 | 220 | 0.00 |
| 2 | 7.00 | 300 | 2.00 |
| FRONT INLET (SPLIT/SPLITLESS) | | | Mode: Splitless |
| Initial temp: | 250° C. (On) | Pressure: | 16.24 psi (On) |
| Purge flow: | 50.0 mL/min | Purge time: | 2.00 min |
| Total flow: | 54.1 mL/min | Gas saver: | On |
| Saver flow: | 20.0 mL/min | Saver time: | 15.00 min |

-continued

| 6890 GC METHOD | | |
|---|---|---|
| Gas type: | Helium | |
| COLUMN 1 | Model Number | Agilent 19091S-133 |
| FRONT DETECTOR | Agilent 5780 FID | |
| MS ACQUISITION PARAMETERS | | |
| Solvent Delay: 2.00 min | Resulting EM Voltage: | 1576.5 |
| Low mass: 35.0 | High Mass: 300.0 | |
| Threshold: 150 | | |
| MS Quad: 150° C. | MS Source: 230° | |

Results of Examples Discussed

Performance of low TFM prototypes for fragrance loss during storage: Fragrance loss during bar storage for one month at 50° C.: It has been known that one problem that leads to low fragrance activity in soap bars is the inherent loss of perfume over time (lack of good retention) during bar storage on shelf/in the warehouse, and during bar use. Applicants have previously noted that up to 75% of the perfume is lost from the surface of a soap bar after 12 weeks of bar storage at room temperature. The loss of fragrance during bar storage can be both physical and chemical. In a typical bar package such as wraps or cartons, fragrance ingredient loss is mostly due to evaporation during bar storage. The relatively high pH of the soap bar also leads to chemical instability of fragrance compounds to a certain extent. Various approaches have been previously investigated in an attempt to retain higher levels of perfume in soap bars, including package options, coating of the bar surface, enhancing the liquid crystalline phase content, preservative types, perfume dosage levels and addition of antioxidant.

Compared to a conventional soap bar, current low TFM prototypes have significant changes in TFM level, liquid crystal content, and water activities in the continuous phase, all of which may play a role in perfume loss during storage. To investigate the fragrance loss during the low TFM bar storage, applicants chose two commercially available perfume mixes, Perfume 1 and Perfume 2. The compositions of these mixes are set fort in Table 2 above. Perfume 1 contains the highest level of top notes (55%). Among the top notes contained in Perfume 1, limonene, which is a hydrophobic compound, is the major component (35%). On the other hand, Perfume 2 is well balanced in top/middle/bottom notes. Perfume 1 and Perfume 2 were thus chosen for the fragrance loss study during storage, where Perfume 1 represents perfume oils of high volatility and high hydrophobicity, and Perfume 2 represents perfume oils of well balanced top/middle/bottom notes.

In Examples 3-6 (Tables 3 and 4), percentage of perfume headspace retention (perfume headspace concentration after storage divided by that of initial time zero) over bar surface after 50° C. storage for one month was plotted. Surprisingly, it was found that, for both fragrance oil mixes (Perfume 1 and Perfume 2), both of the low TFM prototypes (bar prototype A, SL 50 sorbitol and bar prototype B, SL 50 glycerine) exhibited higher percentage of perfume retention compared to the controls, which indicates that SL 50 bars (bar prototype A and B) lose significantly fewer perfume compounds during bar storage at 50° C. The bars have starch-polyol structuring system as noted. Without wishing to be bound by theory, it is believed that polyols (e.g., 5-14%) are good solvents for perfume components in general and may "lock" perfume within the bar matrix and prevent perfume loss during storage.

Fragrance loss during bar storage under wash conditions: In Examples 7-10, retention of perfume (perfume headspace concentration after storage divided by that of initial time zero) was tested after bars were washed twice a day and stored in ambient temperature (⅓ loss of bar original weight, ~20 days of storage). Surprisingly, different from perfume retention during bar storage (as dry bar) noted in Examples 3-6, data in Examples 7-10 indicates that there is no significant difference between perfume retention in low TFM prototypes (bar prototype A and B) vs. that in controls for both fragrance oils (Perfume 1 and Perfume 2) under twice day wash/storage condition. This may be due to the fact that, during wash, bars hydrate and a mush layer forms on the bar surface. Therefore, fragrance loss during bar use/storage seems to exhibit a different trend compared to that of dry bar storage due to changes of the bar matrix on the surface of the bar. It was also noted from the examples that in both storage conditions, Perfume 1 oil (which is rich in perfume ingredients of high volatilities) showed a higher percentage of perfume loss in the same bar prototype compared to that of Perfume 2 (which is well balanced in top/middle/bottom notes). Lower volatile perfume such as Perfume 2 is thus preferred.

What is claimed is:

1. A method for enhancing perfume retention during storage of dry bar which method comprises selecting and formulating perfume into extrudable bar compositions comprising:

a) 20 to less than 55% by wt. fatty acid soap;

b) 0.1 to 2.0%, preferably 0.3 to 1.5% water soluble salt of monovalent cation;

c) 0 to 5.0% fatty acid; and d) structuring system comprising:

i. 5 to 30%, preferably 6 to 25%, even more preferably 8 to 20% by wt. polyol (preferably selected from group consisting of glycerol, sorbitol and mixtures thereof);

ii. 6% to 30%, preferably 6 to 25% by wt. starch; and iii. 0 to 10% by wt. water soluble particles; and wherein said enhanced perfume retention is measured by storing said bar at 50° C. for one month.

2. A method according to claim 1 wherein perfume is of low volatility.

3. A method according to claim 1 wherein perfume is a Type 2 perfume as defined.

4. A method according to claim 1 wherein extrudable bar compositions comprise 0.3 to 1.5% water soluble salt of monovalent cation.

* * * * *

Disclaimer

7,981,852 B2 — Lin Yang, Woodbridge, CT(US); Georgia Shafer, Southbury, CT (US); Ricardo-Neri Da Silva, San Paulo CEP (BR); Sergio Roberto Leopoldino, Sao Paulo (BR). METHOD OF ENHANCING PERFUME RETENTION DURING STORAGE USING LOW TOTAL FATTY MATTER EXTRUDED BARS HAVING STARCH POLYOL STRUCTURING SYSTEM. Patent dated July 19, 2011. Disclaimer filed March 8, 2011, by the assignee, Conopco, Inc.

Hereby enters the term of this patent not to exceed beyond the expiration date of serial number 12/639,113 filed December 16, 2009.

(*Official Gazette September 6, 2011*)